(12) United States Patent
Eaton

(10) Patent No.: US 6,817,170 B2
(45) Date of Patent: Nov. 16, 2004

(54) YARN MONITORING

(75) Inventor: David Charles Eaton, Buxton (GB)

(73) Assignee: Fibrevision Limited, Macclesfield (GB)

( * ) Notice: Subject to any disclaimer, the term of this patent is extended or adjusted under 35 U.S.C. 154(b) by 155 days.

(21) Appl. No.: 10/225,312

(22) Filed: Aug. 21, 2002

(65) Prior Publication Data
US 2003/0037531 A1 Feb. 27, 2003

(30) Foreign Application Priority Data
Aug. 25, 2001 (GB) .............................................. 0120771

(51) Int. Cl.⁷ .......................................... D01H 13/26
(52) U.S. Cl. ........................................ 57/264; 57/265
(58) Field of Search ..................... 57/264, 265; 73/159, 73/160; 356/429, 430, 431

(56) References Cited

U.S. PATENT DOCUMENTS

| | | | |
|---|---|---|---|
| 4,045,659 A | | 8/1977 | Akagawa et al. ......... 235/151.3 |
| 4,168,604 A | * | 9/1979 | Mannhart ..................... 57/264 |
| 4,887,155 A | | 12/1989 | Massen ...................... 358/107 |
| 5,119,308 A | * | 6/1992 | Samoto ....................... 700/139 |
| 5,181,374 A | | 1/1993 | Aeppli ........................ 57/264 |
| 5,748,481 A | * | 5/1998 | Nakade ....................... 700/143 |
| 6,038,021 A | * | 3/2000 | Piso et al. ................ 356/238.2 |
| 6,219,135 B1 | * | 4/2001 | Hensel et al. ............ 356/238.2 |

FOREIGN PATENT DOCUMENTS

| | | | | |
|---|---|---|---|---|
| EP | 457450 A1 | * | 11/1991 | .......... G01N/33/36 |
| EP | 0976855 A1 | | 2/2000 | |

* cited by examiner

Primary Examiner—John J. Calvert
Assistant Examiner—Shaun R Hurley
(74) Attorney, Agent, or Firm—Baker Botts L.L.P.

(57) ABSTRACT

A method of and apparatus for monitoring the processing of a multifilament yarn to indicate a number of protrusions in the yarn is provided. In this method, a multifilament yarn is passed through a light beam directed from a light emitting device to a light receiving device, and the amount of light received by the light receiving device is measured at predetermined time intervals. From the measured amounts of light over a predetermined time period a measuring and computing device produces a frequency distribution, and a threshold level representative of an ideal yarn is calculated from the frequency distribution. The number of measurements that fall outside that threshold level is recorded and is indicative of the number of filament breaks and loops in the yarn.

12 Claims, 3 Drawing Sheets

YARN MONITORING

FIELD OF THE INVENTION

This invention relates to the monitoring of yarn whilst it is being processed, and in particular to the monitoring of the regularity of a multifilament yarn in order to detect broken filaments or protruding filament loops.

BACKGROUND OF THE INVENTION

During the processing of a multifilament yarn it is possible that filaments become broken or filament loops are formed. Such broken filaments or loops tend to protrude from the surface of the yarn, thereby reducing the efficiency of the subsequent processes performed on the yarn, such as warping, knitting, weaving. The broken filaments or loops subsequently protrude from the surface of a fabric made from that yarn, which reduces the quality and appearance of the fabric. It is therefore desirable to monitor the occurrence of protruding broken filaments or loops during the processing of the yarn so that unacceptable yarn may be rejected instead of being made up into an unsatisfactory fabric. Such monitoring also serves to draw attention to factors during the processing of the yarn that affect the incidence of broken filaments or loops, so that attempts can be made to change the processing parameters or modify the apparatus in order to reduce the number of broken filaments or loops and produce an ideal yarn. By ideal yarn is intended to mean a yarn without any broken filaments or filament loops protruding to an unacceptable level from the surface of the yarn.

Two principal methods of monitoring the processing of multifilament yarns for broken filaments or protruding filament loops are currently in operation. In the first method, a light beam is directed adjacent the surface of the moving yarn as it is being processed. If a broken filament or filament loop protrudes from the surface of the yarn it is likely to intrude briefly into the light beam and the amount of light received by a receiving device is temporarily reduced. In the second method, a light beam is directed at the moving yarn during processing, the light passing either side of the yarn being received by a receiving device. If a broken filament or filament loop protrudes from the surface of the yarn, the effective cross-sectional area of the yarn in the light beam is briefly increased and again the amount of light received by a receiving device is temporarily reduced. With both methods, the number of such reductions in the amount of light received in a given time, corresponding with the passage of a given length of yarn, is recorded. This indicates the number of broken filaments or loops per unit length of yarn.

In the case of the first method, detection of a broken filament or filament loop is achieved only if that filament protrudes from the surface of the yarn in a plane such that it intrudes into the light beam. Also, the clearance between the light beam and the surface of the yarn is critical, and has to be altered for different yarns since the regularity of the 'cylindrical surface' presented by the yarn is dependent on the type of yarn, the twist level, and/or the degree of texturing, interlacing and the like. In an attempt to overcome the first problem, the light beam may be directed adjacent the yarn as it passes around a roller, so that the broken filaments or filament loops tend to be directed outwardly into the light beam. However any broken filaments or filament loops that become trapped between the yarn and the roller are not detected. This problem occurs to a far lesser extent with the second method. However, a comparable second problem exists, in that it is difficult to set the tolerance or 'threshold level' for the amount of light being received by the receiving device before a broken filament or filament loop is recorded due to the above mentioned non-regularity of the 'cylindrical surface' presented by the yarn. The setting may even have to be adjusted from position to position on a single yarn processing machine or even with time on a single position, due to variation in local contamination, optical qualities of the light emitting and receiving devices and other local factors.

With either method, the detection of broken filaments in practical thread-lines is often made more difficult due to unavoidable disturbances to the thread-line. These are caused, for example, by longitudinal "pulsing" of the yarn before and after an interlace jet, or by transverse vibration of the yarn as it is delivered at high speed through the processing apparatus.

OBJECT OF THE INVENTION

It is an object of the present invention to provide, whilst monitoring the protrusions, i.e. protruding broken filaments or loops, in a multifilament yarn during the processing thereof, a method of adjustment of the threshold level in order to overcome to a significant extent the problems associated with the second method as currently used. In addition, the invention seeks to distinguish the effects of the above-described disturbances on the shadowed yarn signal from those of broken filaments.

SUMMARY OF THE INVENTION

The invention provides a method of monitoring the processing of a multifilament yarn, in which a light beam is directed from a light emitting device to a light receiving device, a multifilament yarn is passed through the light beam and the amount of light received by the light receiving device is measured, comprising measuring the amount of light received at predetermined time intervals, producing a frequency distribution from the measured amounts of light over a predetermined time period, calculating from the frequency distribution a threshold level representative of an ideal yarn, and recording the number of measurements that fall outside that threshold level to indicate the number of protrusions in the yarn.

The predetermined intervals may be such that measurements are recorded at between 10000 and 50000 times per second depending on process speed, e.g. substantially 25000 times per second. The predetermined time period may be between 10 and 1000 milliseconds, preferably substantially 100 milliseconds.

The calculation may comprise calculating a normal value, which is that measurement within which a predetermined number of the measurements fall. The predetermined number may be between 95% and 100%, and may be 99%. When discontinuous samples of signal are used to form the distribution, it may be necessary for the method to comprise recording the normal values of a plurality of distributions and taking the mean or minimum value of such distributions. The calculation may also include adjusting the normal value by a sensitivity factor to determine the threshold level. The sensitivity factor may be between 1% and 50% of the normal value, depending on the size of the broken filaments or loops to be recorded.

The method may also include differentiating, by analogue or digital means, the measured amounts of light with respect to time. The differentiation may include determining the first derivative of the measured amounts of light, from which the frequency distribution is produced.

The invention also provides apparatus for monitoring the processing of a multifilament yarn, comprising a light emitting device operable to direct a light beam to a light receiving device operable to measure the amount of light received, further comprising a measuring and computing device operable to:

measure the amount of light received at predetermined intervals;

produce over a predetermined time period a frequency distribution of the measured amounts of light;

calculate from the frequency distribution a threshold level representative of an ideal yarn, and;

record the number of measurements that fall outside the threshold level to indicate the number of protrusions in the yarn.

The measuring and computing device may be operable to measure the amount of light received at between 10000 and 50000 times per second depending on process speed, e.g. substantially 25000 times per second. The measuring and computing device may be operable to produce a frequency distribution of the measured amounts of light over a time period of between 10 and 1000 milliseconds, preferably substantially 100 milliseconds.

The measuring and computing device may be operable to calculate a normal value, which is that measurement within which a predetermined number of the measurements fall. The predetermined number may be between 95% and 100%, and may be 99%. The measuring and computing device may record the "normal values" of several distributions and take the mean or minimum values to get a true representation of the complete signal. The measuring and computing device may also be operable to adjust the normal value by a sensitivity factor to determine the threshold level. The sensitivity factor may be between 1% and 50% of the basic measurements.

The measuring and computing device may be operable to determine the first derivative of the measured amounts of light, from which the frequency distribution is produced.

BRIEF DESCRIPTION OF THE DRAWINGS

The invention will now be further described with reference to the accompanying drawing in which.

DESCRIPTION OF THE PREFERRED EMBODIMENTS

Figure 1:
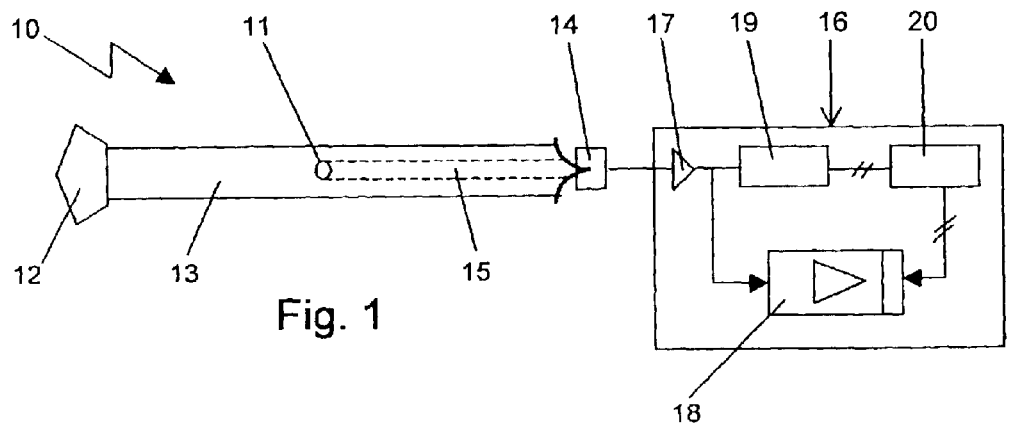
FIG. 1 shows a monitoring apparatus for a single yarn.

Referring now to FIG. 1, there is shown apparatus 10 for monitoring the processing of a single multifilament yarn 11. The apparatus 10 comprises a light emitting diode 12, which directs a beam of light 13 to a light receiving diode 14. The diodes 12 and 14 are positioned so that the beam of light 13 impinges on the running yarn 11, which casts a shadow 15 on the light receiving diode 14. If the yarn 11 is of constant diameter, the amount of light received by the diode 14 will be constant. However, if a section of yarn 11 having a broken filament or filament loop extending from its surface passes through the beam of light 13, the amount of light received by the diode 14 at that instant will be reduced. A device 16 receives a signal from the light receiving diode 14 proportional to the amount of light received by the diode 14. If, as in the known arrangement described above, device 16 were such that it simply measures the signal and counts the number of reduced measurements representing the broken filaments or filament loops, such an arrangement would perform the conventional second method referred to above. However, due to the degradation over a period of time of the signal received by the device 16 as a result of contamination effects, for example oil splashes, the threshold value representing an ideal yarn will diminish. This can lead to inaccuracies in recording the number of filament breaks or loops present in the yarn.

Figure 2:
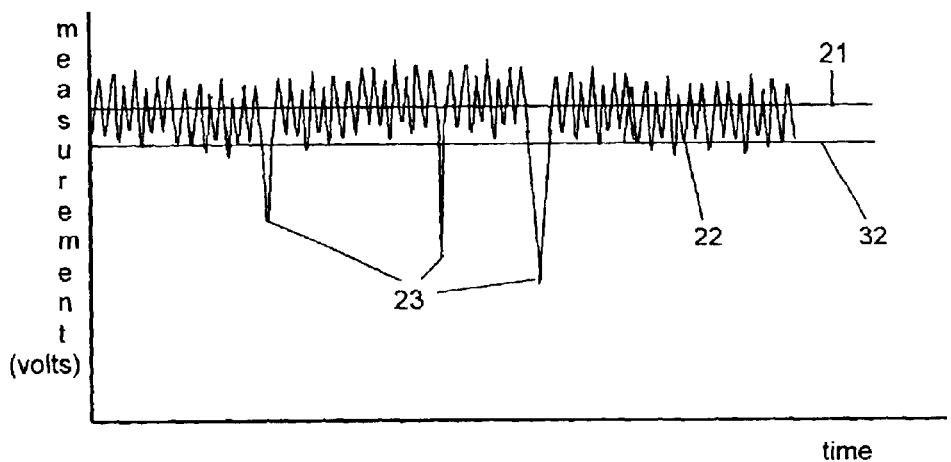
FIG. 2 is a graph of measurements taken over a period of time.
Figure 3:
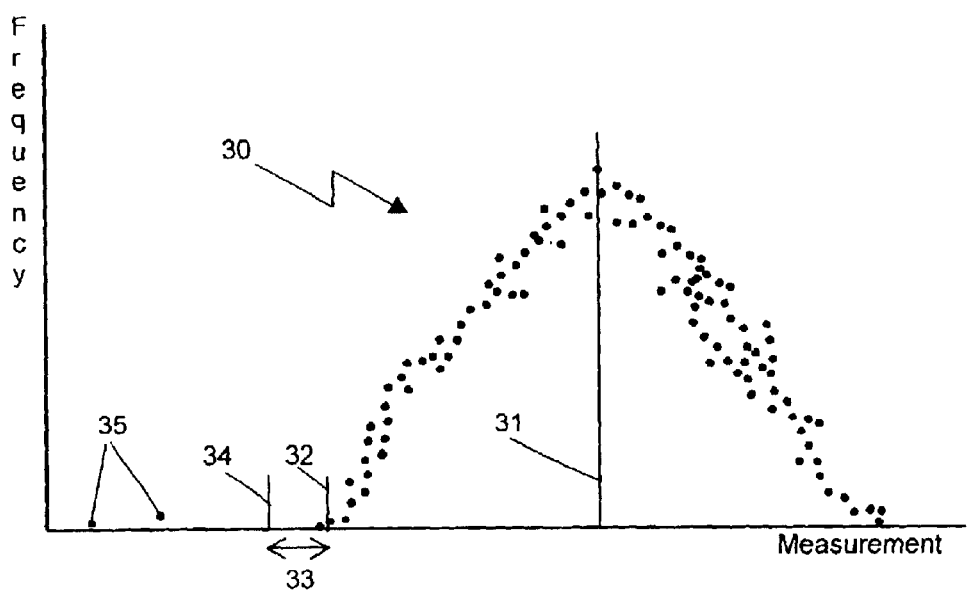
FIG. 3 shows a frequency distribution produced from the measurements taken.

To overcome this problem, in this case the device 16 is a measuring and computing device, which is operable to measure, and record the amount of light received by the diode 14 at predetermined intervals between 10000 and 50000 times per second depending on process speed, for example 25000 times per second. The signals from the diode 14 are passed to an amplifier 17 and then to an analogue detector 18. The amplified signals are also passed to an analogue/digital converter 19, which forwards digital signals to a microprocessor 20. In the case of a perfect cylinder, all of the measurements would be the same as shown by line 21 in FIG. 2. However, the actual measurements will show variations since the diameter of a textile yarn 11 varies along its length with the type of yarn, twist level, degree of texturing, interlacing or other process parameters, as shown by line 22 in FIG. 2. The microprocessor 20 produces a frequency distribution 30, in this case directly from the measurements, as shown in FIG. 3. From the frequency distribution 30 it will be seen that the recorded measurements that occur with the greatest frequency are distributed around a measurement 31 representing the nominal diameter of the yarn 11. Since the diameter of a textile yarn 11 is not constant for the reasons mentioned above, measurements above and below the measurement 31 occur, with reducing frequency for those measurements differing from the measurement 31 by greater amounts.

From the frequency distribution 30, the microprocessor 20 calculates the normal value 32 over a predetermined period of time, for example 100 milliseconds. The normal value 32 may be regarded as the value above which a predetermined number of the measurements fall, e.g. above which 99% of the measurements fall. When discontinuous samples of signal are used to form the distribution, it may be necessary for the method to comprise recording the normal values of a plurality of distributions and taking the mean or minimum value of such distributions. So as not to record as representing a broken filament or filament loop those readings falling only just outside the normal value 32, for example because of contamination and other local or transitory factors, the normal value 32 is adjusted by a sensitivity factor 33 to produce a threshold value 34 for that time period, shown in FIGS. 2 and 3. This threshold value 34 is transmitted to the analogue detector 18, which continuously compares the amplified signal from the light-receiving device 16 with the current threshold value 34. The line 22 also exhibits measurements at 23 (FIG. 2), occurring at frequencies shown at 35 (FIG. 3), representing the passage through the light beam 13 of a broken filament or filament loop protruding from the surface of the yarn 11. These measurements 23 fall outside the calculated threshold value and are counted.

Since the normal value 32 is calculated with reference to the variation of actual measurements recorded for the yarn 11 being processed during a particular time period, the apparatus 10 is suitable for use with any type of yarn 11 having any twist level, and/or the degree of texturing, interlacing and the like. The value of the sensitivity factor 33 may be adjusted to cater for yarns having greater or lesser diameter variation in their ideal state. In addition, the threshold value 34 is calculated for successive periods of time so that any variation in signal strength with time is compensated for.

Figure 4:
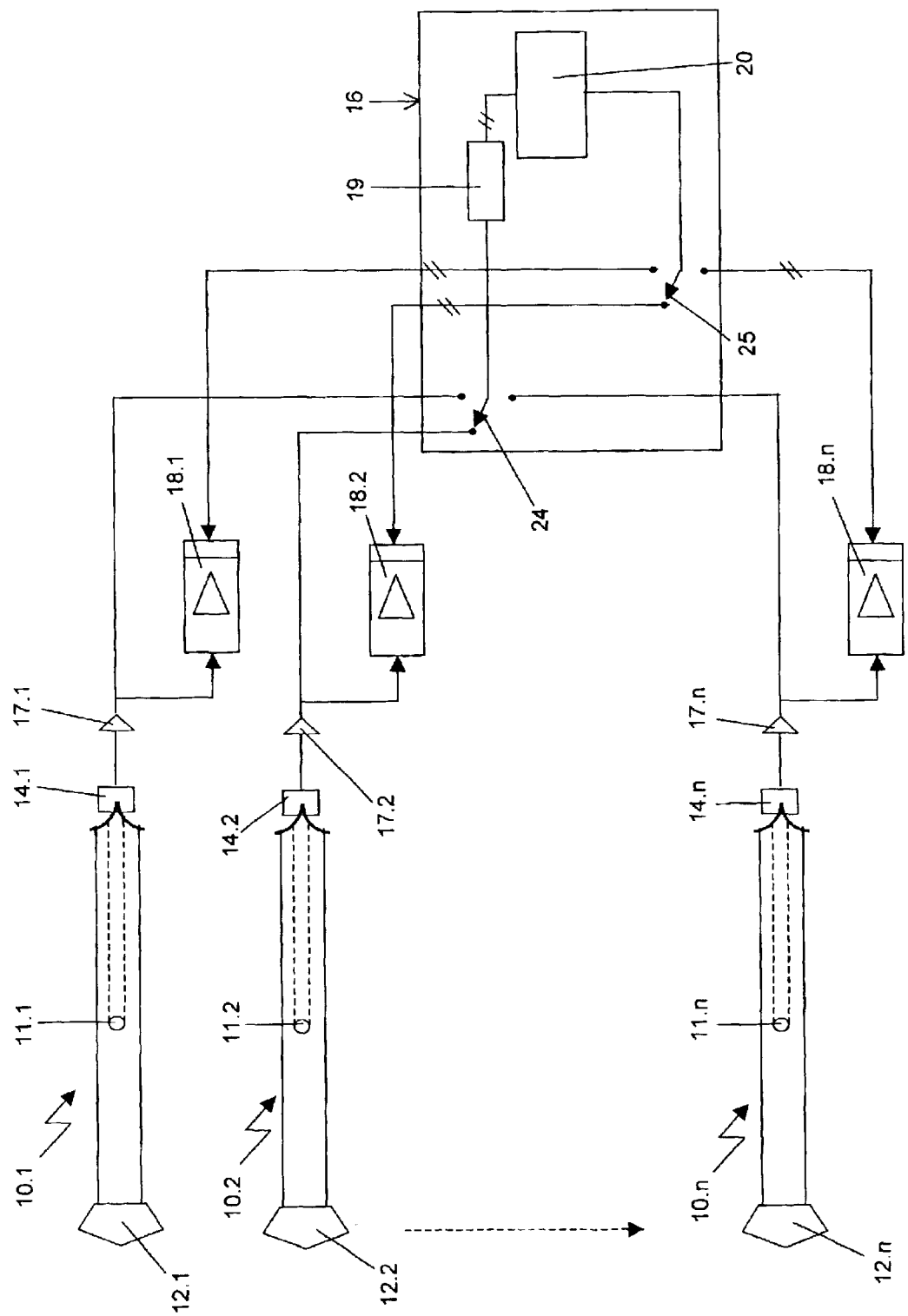
FIG. 4 shows the monitoring apparatus in multi-position textile machine.

In the case of a multi-position textile machine processing many yarns, the apparatus is shown in FIG. 4. For each yarn 11.1, 11.2 . . . 11.n there is a corresponding apparatus 10.1, 10.2 . . . 10n which comprises a light emitting diode 12.1, 12.2 . . . 12.n, and a light receiving diode 14.1, 14.2 . . . 14.n. The signals from the diodes 14.1, 14.2 . . . 14n are passed to respective amplifiers 17.1, 17.2 . . . 17.n. and then to respective analogue detectors 18.1, 18.2 . . . 18.n. The amplified signals are also passed via a multiplexer switch 24 successively to the analogue/digital converter 19, which forwards digital signals to a microprocessor 20. The microprocessor 20 produces a frequency distribution 30 of the measurements for each of the yarn positions in turn, and respective calculations of the normal values 32 and threshold values 34 over a predetermined period of time. Each threshold value 34 is transmitted via a second multiplexer switch 25 successively to the respective analogue detector 18.1, 18.2 . . . 18.n, which continuously compares the amplified signal from the light receiving device 16 with the threshold value 34 last transmitted to it.

Figure 5:
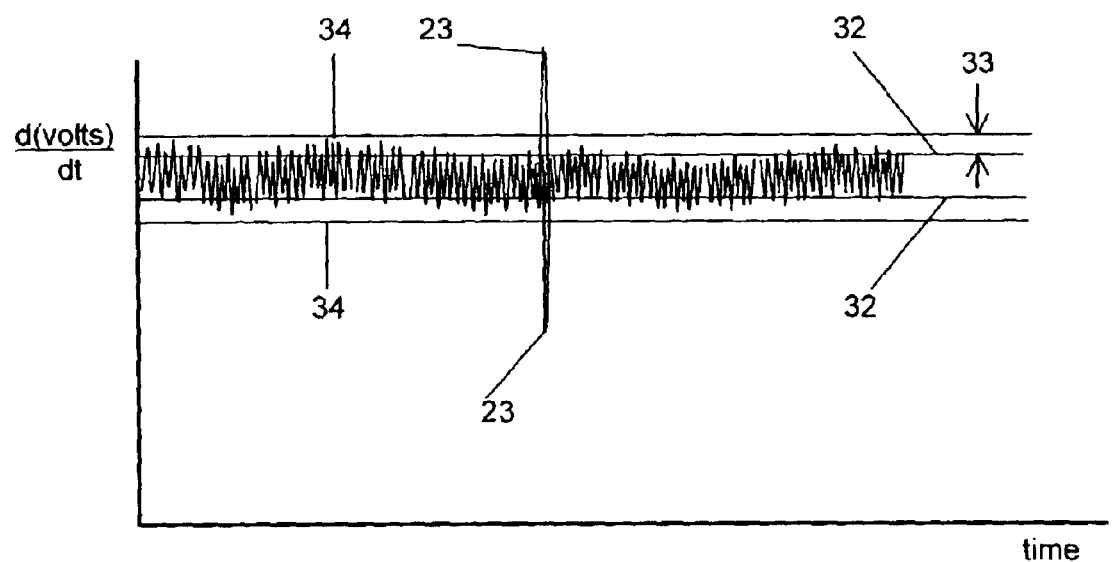
FIG. 5 is a graph of the first derivative of the measurements of FIG. 2

The main feature of a broken filament, compared with these other disturbances, is that it's effect on the light signal of the detector is very brief since the filament is carried past the sensor at the speed of the yarn. In high-speed processes (>2000 m/min) the time for a broken filament to cross the entire field of the optics is measured in microseconds. This means that the base frequency of a passing filament is measured in kHz and any rising or falling edges are measured in tens of kHz. Frequencies associated with yarn vibration and jet pulsing tend to be much lower than this, perhaps a few hundred Hz at the most and often much lower. Because of this, for high speed processes (>2000 m/min yarn throughput speed), the rapid change of measurement due to the high speed passage of a broken filament through the light beam 13, the measuring and computing device 16 determines, by analogue or digital means, the first derivative of the readings shown in FIG. 2, and this is shown in FIG. 5. In FIG. 2, several large disturbances 23 can be seen as well as many smaller ones. In a high speed process, the single, short duration dip 23 at the centre of the trace in FIG. 2 is caused by a broken filament whereas the other large but longer duration disturbances are effectively noise, caused by the vibration and pulsing present in high speed processing as described previously. FIG. 5 shows the first derivative of the data in FIG. 2. It can be seen that the longer duration disturbances 23, i.e. those with smaller rates of change of measurement, have been eliminated. However, the short duration disturbance 23 with the larger rates of change of measurement at the centre of the trace, which is due to a broken filament, is clearly discernible. From these first derivative values shown in FIG. 5, the frequency distribution as shown in FIG. 3 is produced by the microprocessor 20, and the normal and threshold values 32, 34 are calculated from the frequency distribution as described above. The microprocessor 20 records the number of first derivative values 35 higher than the predetermined threshold value 34.

As an alternative to detecting broken filaments, the apparatus 10 may be used to measure the regularity of twist, interlace or the like in the yarn 11. By suitable choice of the predetermined number used in the calculation of the basic measurements 32, and reducing the sensitivity factor 33 to a small value, small changes in diameter of the yarn 11 due to variations in twist, interlace or the like may be detected and recorded. In consequence the same apparatus 10 may be used for recording either broken filaments or process quality, i.e. yarn regularity, as desired.

What is claimed is:

1. A method of monitoring the processing of a multifilament yarn, in which a light beam is directed from a light emitting device to and is received by light receiving device, a multifilament yarn is passed through the light beam and the amount of light received by the light receiving device is measured, comprising measuring the amount of light received by the light receiving device at predetermined time intervals such that measurements are recorded at between 10000 and 50000 times per second, producing a frequency distribution from the measured amounts of light over a predetermined time period, calculating from the frequency distribution a threshold level representative of an ideal yarn, and recording the number of measurements that fall outside that threshold level to indicate a number of protrusions in the yarn.

2. The method according to claim 1, wherein the predetermined time intervals are such that measurements are recorded substantially 25000 times per second.

3. The method according to claim 1, wherein the predetermined time period is between 10 and 1000 milliseconds.

4. The method according to claim 1, wherein the calculation comprises calculating a normal value, which is that measurement within which a predetermined number of the measurements fall.

5. The method according to claim 4, wherein the predetermined number is between 95% and 100%.

6. The method according to claim 4, comprising recording the normal values of a plurality of distributions and wherein the calculation comprises taking the mean or minimum value of such distributions.

7. The method according to claim 4, wherein the calculation also includes adjusting the normal value by a sensitivity factor to determine the threshold level.

8. The method according claim 7, wherein the sensitivity factor is between 1% and 50% of the normal value.

9. The method according to claim 1, wherein the calculation comprises determining the first derivative with respect to time of the measured amounts of light, from which the frequency distribution is produced.

10. A method of monitoring the processing of a multifilament yarn, in which a light beam is directed from a light emitting device to and is received by a light receiving device, a multifilament yarn is passed through the light beam and the amount of light received by the light receiving device is measured, comprising measuring the amount of light received by the light receiving device at predetermined time intervals, producing a frequency distribution from the measured amounts of light over a predetermined time period, calculating from the frequency distribution a threshold level representative of an ideal yarn, and recording the number of measurements that fall outside that threshold level to indicate a number of protrusions in the yarn, wherein the calculation comprises calculating a normal value, which is that measurement within which a predetermined number of the measurements fall, and wherein the calculation also includes adjusting the normal value by a sensitivity factor to determine the threshold level.

11. The method according to claim 10, wherein the sensitivity factor is between 1% and 50% of the normal value.

12. A method of monitoring the processing of a multifilament yarn, in which a light beam is directed from a light emitting device to and is received by a light receiving device, a multifilament yarn is passed through the light beam and the amount of light received by the light receiving device is measured, comprising measuring the amount of light received by the light receiving device at predetermined time intervals, producing a frequency distribution from the measured amounts of light over a predetermined time period, calculating from the frequency distribution a threshold level representative of an ideal yarn, and recording the number of measurements that fall outside that threshold level to indicate a number of protrusions in the yarn, wherein the calculation comprises determining the first derivative with respect to time of the measured amounts of light, from which the frequency distribution is produced.

* * * * *